United States Patent
Jeffrey et al.

(10) Patent No.: US 11,020,555 B2
(45) Date of Patent: Jun. 1, 2021

(54) TUBE INTRODUCERS, ASSEMBLIES AND METHODS

(71) Applicant: SMITHS MEDICAL INTERNATIONAL LIMITED, Ashford (GB)

(72) Inventors: Andrew Thomas Jeffrey, Hythe (GB); Christopher John Woosnam, Great Sutton (GB)

(73) Assignee: Smiths Medical International Limited, Ashford (GB)

( * ) Notice: Subject to any disclaimer, the term of this patent is extended or adjusted under 35 U.S.C. 154(b) by 492 days.

(21) Appl. No.: 15/580,094

(22) PCT Filed: May 31, 2016

(86) PCT No.: PCT/GB2016/000109
§ 371 (c)(1),
(2) Date: Dec. 6, 2017

(87) PCT Pub. No.: WO2016/207583
PCT Pub. Date: Dec. 29, 2016

(65) Prior Publication Data
US 2018/0169364 A1    Jun. 21, 2018

(30) Foreign Application Priority Data

Jun. 24, 2015   (GB) ...................................... 1511113

(51) Int. Cl.
*A61M 16/04* (2006.01)
*A61M 25/06* (2006.01)

(52) U.S. Cl.
CPC .... *A61M 16/0465* (2013.01); *A61M 16/0488* (2013.01); *A61M 25/0662* (2013.01); *A61M 2209/06* (2013.01)

(58) Field of Classification Search
CPC .......... A61M 16/0465; A61M 16/0488; A61M 25/0662; A61M 2209/06
See application file for complete search history.

(56) References Cited

U.S. PATENT DOCUMENTS 3,363,629 A * 1/1968 Kuhn .................... A61M 16/04
                                                          128/207.15
4,211,234 A * 7/1980 Fisher ............... A61M 16/0488
                                                          128/200.26
(Continued)

FOREIGN PATENT DOCUMENTS

AT           146305 B    6/1936
EP         1281414 A1    2/2003
(Continued)

OTHER PUBLICATIONS

PCT International Search Report and Written Opinion, PCT/GB2016/000109, EPO dated Jul. 26, 2016.

*Primary Examiner* — Bradley H Philips
*Assistant Examiner* — Savannah L Gabriel
(74) *Attorney, Agent, or Firm* — Louis Woo

(57) ABSTRACT

A tracheostomy tube introducer (1) has a patient end region (10) on which the tube (2) is mounted and that is curved in one sense. The introducer has a machine end region (11) projecting from the rear end of the tube (2) to provide a handle that curves in the opposite sense to the patient end region (10) so that the introducer has an S shape along its length. A bore (24) for a guide member extends from the patient end tip (14) of the introducer and opens in the machine end region (11) through a side opening (25). The introducer 1 is provided in a kit (200) with the tracheostomy tube (2) and a dilator (202) having the same general S shape as the introducer.

8 Claims, 4 Drawing Sheets

(56) References Cited

U.S. PATENT DOCUMENTS

| | | | | |
|---|---|---|---|---|
| 4,340,046 A | | 7/1982 | Cox | |
| 5,058,580 A | * | 10/1991 | Hazard | A61M 16/0472 128/207.15 |
| 5,277,178 A | * | 1/1994 | Dingley | A61M 16/0409 128/200.26 |
| 5,507,279 A | * | 4/1996 | Fortune | A61M 16/0472 128/200.26 |
| 5,873,362 A | * | 2/1999 | Parker | A61M 16/04 128/207.14 |
| 6,146,402 A | * | 11/2000 | Munoz | A61B 1/0607 606/194 |
| 7,552,729 B2 | * | 6/2009 | O'Mara | A61M 16/0488 128/200.26 |
| 8,202,289 B2 | * | 6/2012 | Woo | A61M 29/00 606/185 |
| 2009/0312784 A1 | * | 12/2009 | Tupper | A61M 16/0472 606/191 |
| 2009/0320833 A1 | * | 12/2009 | Cuevas | A61M 16/0472 128/200.26 |
| 2010/0275911 A1 | | 11/2010 | Arlow et al. | |
| 2012/0017913 A1 | * | 1/2012 | Schumacher | A61M 16/0488 128/207.14 |

FOREIGN PATENT DOCUMENTS

| | | | |
|---|---|---|---|
| GB | 2310605 A | 9/1997 | |
| WO | 2006/087512 A1 | 8/2006 | |
| WO | WO-2006087512 A1 * | 8/2006 | A61B 17/3415 |
| WO | 2014/118172 A1 | 8/2014 | |

* cited by examiner

TUBE INTRODUCERS, ASSEMBLIES AND METHODS

FIELD OF THE INVENTION

This invention relates to introducers of the kind adapted for insertion within the bore of a medico-surgical tube, the introducer having a tapering patient end adapted to extend beyond the patient end of the tube and a machine end adapted to extend beyond the machine end of the tube to provide a machine end portion by which the introducer can be gripped when inserted in the tube.

BACKGROUND OF THE INVENTION

In various medical and surgical procedures it is necessary to introduce a plastics tube into the body through a natural or surgically-created opening. It is often desirable for the tube to be flexible in order to conform to the anatomy of a body passage or to reduce trauma to patient tissue. Flexible tubes are more difficult to insert by themselves so it is often necessary to support the tube internally by a stiffer introducer or obturator that can be removed once the tube has been inserted. One example of a procedure where introducers or obturators are used to support a tube is in the insertion of a tracheostomy tube where the tube is inserted through a surgically-made opening into the trachea so that the patient end of the tube locates in the trachea and its opposite, machine end projects outwardly from the surface of the neck. It is important in this procedure that the introducer provides sufficient support to enable the tube to be pushed through the opening between relatively stiff tracheal cartilages but it is also important that the introducer can be inserted easily and quickly since air flow to and from the patient's respiratory passages will be prevented or substantially reduced until the tube has been fully inserted. Examples of introducers or obturators used to insert tracheostomy tubes are described in EP1281414, WO2006/087512, WO2008/113985, GB1502064.7, U.S. Pat. No. 5,222,487, U.S. Pat. No. 5,043,475, EP0371752, U.S. Pat. No. 4,502,482, GB2084023, U.S. Pat. No. 5,928,198, U.S. Pat. No. 6,286,509, EP1099451 and U.S. Pat. No. 6,481,436.

The procedure for forming a tracheostomy may involve the use of one or more dilators after initially forming a narrow passage into the trachea by a needle. The dilator is used to expand the passage formed by the needle sufficiently to allow the tube and introducer to be inserted. Where a single dilator is used this may be curved and tapered. A dilator with enhanced ergonometrics may be used having an S-shape curve along its length, as described in U.S. Pat. No. 8,202,289 and U.S. Pat. No. 8,372,107.

It is an object of the present invention to provide an alternative tube introducer, assembly and method of introducing a tube.

BRIEF SUMMARY OF THE INVENTION

According to one aspect of the present invention there is provided a tube introducer of the above-specified kind, characterised in that at least a part of the introducer has an S shape with a patient end region curved in one sense and a machine end region forming a smoothly continuous curve with the patient end region but in the opposite sense.

The introducer preferably has a bore extending along a part of the length of the introducer and opening towards the machine end through a side opening. The side opening is preferably on the outside of the curve of the machine end region. The patient end region preferably includes along most of its length a shaft with an enlarged portion at a location along its length to centralise the introducer within the bore of the tube in which it is inserted.

According to another aspect of the present invention there is provided an assembly of a tube and an introducer according to the above one aspect of the invention, the introducer being inserted within the tube.

The tube is preferably a tracheostomy tube.

According to a further aspect of the present invention there is provided a kit of components for use in a tracheostomy procedure including a tracheostomy tube, an introducer according to the above one aspect of the present invention and a dilator adapted to enlarge a passage into the trachea prior to insertion of an assembly of the tracheostomy tube and introducer, characterised in that the dilator has an S shape of the same general form as that of the introducer.

According to a fourth aspect of the present invention there is provided a method of introducing a tracheostomy tube including the steps of surgically forming a passage from the surface of the neck through neck tissue into the trachea, positioning a guide member to extend along the passage with one end protruding externally, sliding an S-shape dilator along the guide member to dilate the passage, removing the dilator, sliding an assembly according to the above other aspect of the present invention along the guide member and then removing the introducer and guide member to leave the tube in position with its patient end in the trachea.

BRIEF DESCRIPTION OF THE DRAWINGS

An introducer, assembly and kit and their method of use in a tracheostomy procedure, all according to the present invention, will now be described, by way of example, with reference to the accompanying drawings, in which.

DETAILED DESCRIPTION OF THE INVENTION

Figure 1:
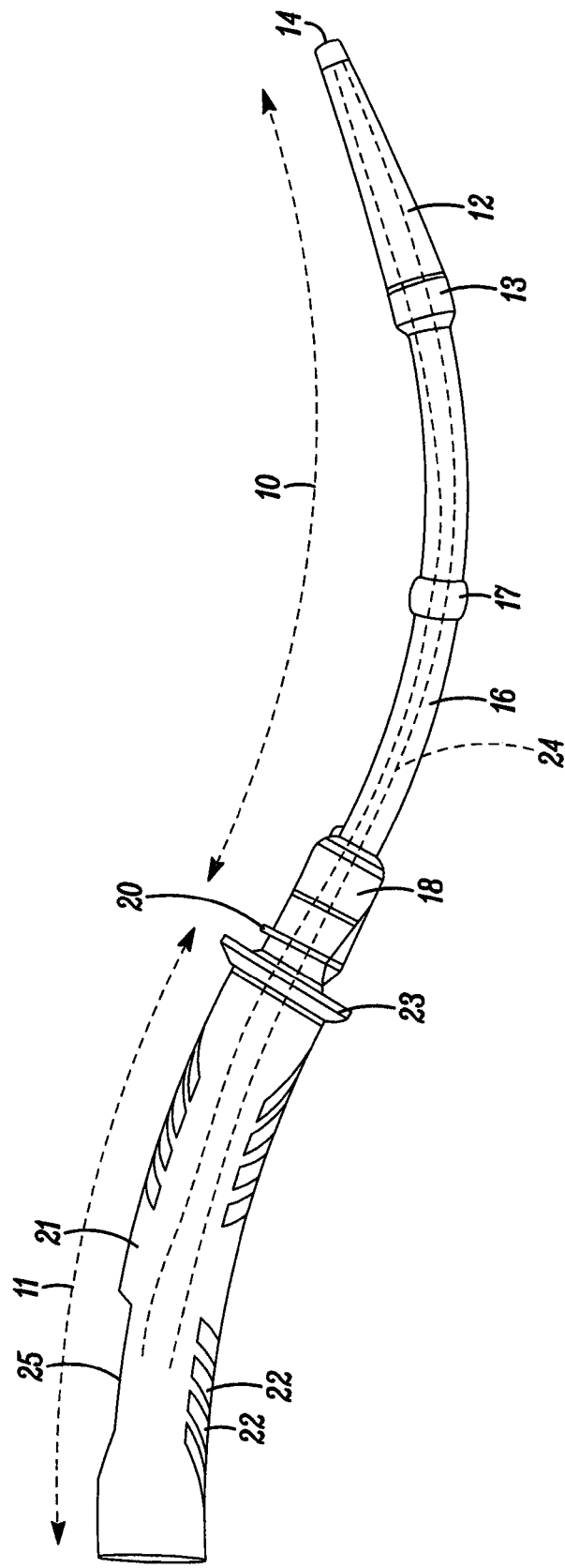
FIG. 1 is a side elevation view of the introducer.
Figure 2:
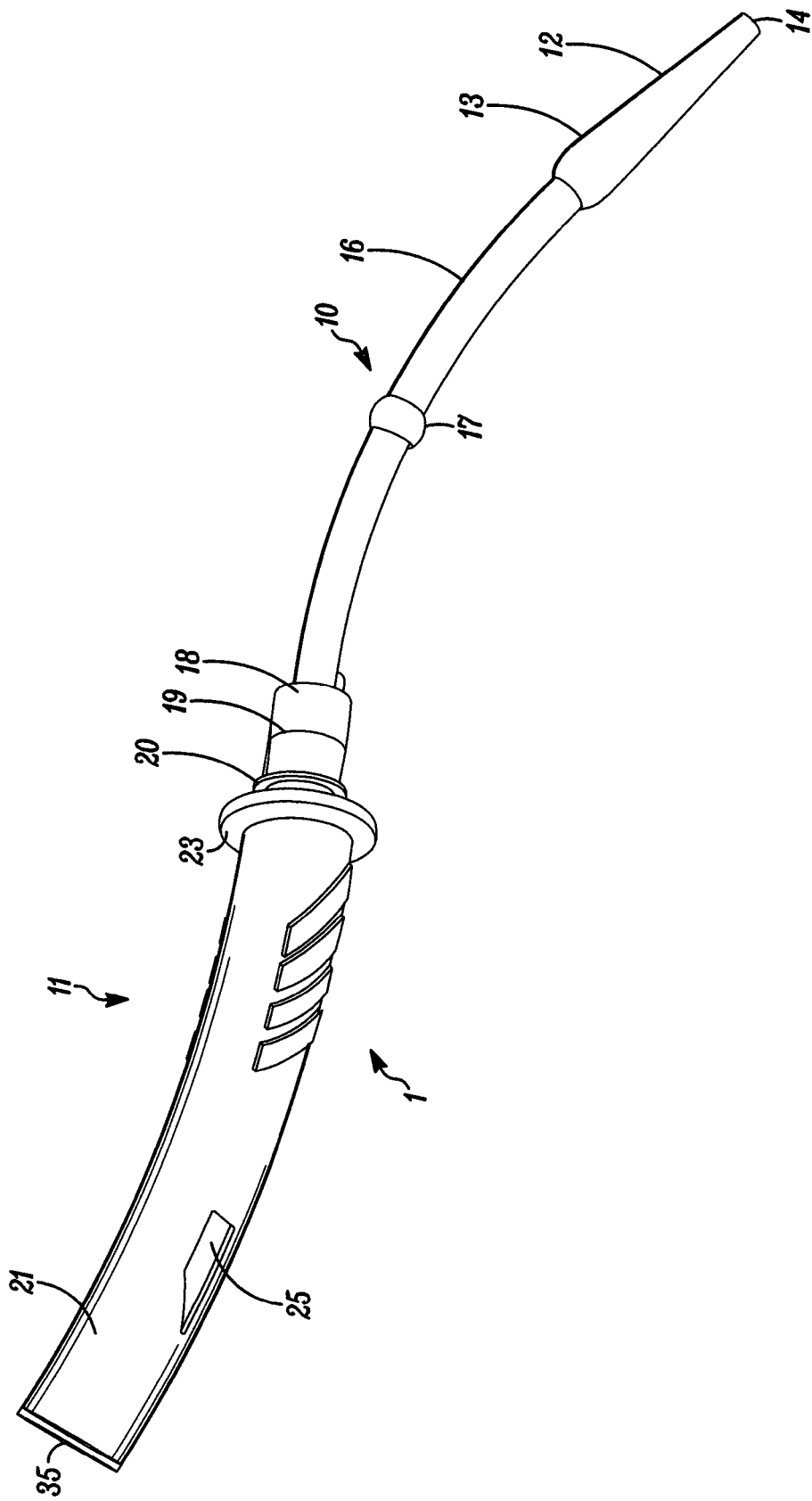
FIG. 2 is a perspective view of the introducer.

With reference first to FIGS. 1 and 2 there is shown an introducer 1 for use in inserting a tracheostomy tube 2 (FIG. 3) through a passage formed through neck tissue into the trachea. The term "introducer" is used herein also to include any device inserted within a tube to help insertion of the tube into the body and includes obturators. The introducer 1 is typically about 212 mm long, although it could have different lengths according to the size of the tube with which it is used, and it has a generally S shape. More particularly, the introducer 1 has a forward or patient end region 10 that is curved along its length with a constant radius of curvature. The rear or machine end region 11 of the introducer 1 forms a smooth continuation of the curve of the forward region 10 but is curved in the opposite sense, that is, its centre of curvature is on the opposite side of the introducer to that of the forward region. The length of the patient end region 10 and the machine end region 11 are approximately equal. The introducer 1 is moulded from a rigid plastics material and, more particularly its forward region 10 is of a polyurethane and its rear region 11 is of a polypropylene, such that its forward end is slightly more flexible than its rear end.

Alternative introducers could include one or more metal components to increase stiffness along the entire introducer or along a part of its length.

The patient end region 10 is, in use, inserted in the tracheostomy tube 2 and has a nose portion 12 at its forward end that tapers along its length from its rear end 13 to its forward end tip 14. The diameter of the rear end 13 is approximately the same as the internal diameter of the tracheostomy tube 2 with which the introducer is used so that it is a close fit within it. The forward end tip 14 has a smaller diameter than the rear end 13, typically about half its diameter. The length of the nose portion 12 is about ten times the diameter of its rear end 13. The major part of the length of the patient end region 10 is provided by a shaft 16 that has a constant diameter along most of its length that is approximately equal to the diameter of the nose portion 12 about midway along its length. The shaft 16 has an enlarged part-spherical bead formation 17 midway along its length. The external diameter of the bead formation 17 is slightly less than the internal diameter of the tube 2 with which the introducer 1 is used. The purpose of the bead formation 17 is to centralise the introducer 1 within the bore of the tube 2 and thereby reduce friction between the introducer and the tube when it is being inserted and removed. The rear end of the shaft 16 is enlarged in diameter to form a cylindrical boss 18 the diameter of which is slightly less than the internal diameter of the hub or connector at the machine end of the tube 2 with which the introducer 1 is used. A shallow groove 19 extends around the outside of the boss 18 about half way along its length to help lock the tracheostomy tube connector 102 (FIG. 3) to the introducer 1. A shallow annular rib 20 extends around the rear end of the boss 18 to engage the rear end of the hub on the tube 2.

The machine end region 11 of the introducer 1 is formed along the major part of its length by a curved handle 21 of circular section with a diameter about three times that of the shaft 16. The surface of the handle 21 is formed with raised or recessed surface formations 22 to improve the grip on the handle. The forward end of the handle 21 is formed with an enlarged outwardly-extending flange 23, which serves to prevent the user's hand slipping forwardly and makes it easier for the user to apply a forwardly-directed force when inserting the tube 2 through tracheal tissue.

The introducer 1 is hollow along part of its length having a bore 24 extending along the shaft 16 and opening at the tip 14 of the nose portion 12. The bore 24 continues into the handle 21 but is closed at its machine end by a plug 35 inserted in its machine end. The bore 24 instead opens on the side of the handle 20 through an opening 25 on the outside of the curvature of the rear portion 11. The bore 24 and opening 25 enable a guide member such as a guidewire to be extended along the introducer 1 so that it can be slid forwardly along the guidewire into the tracheostomy.

Figure 3:
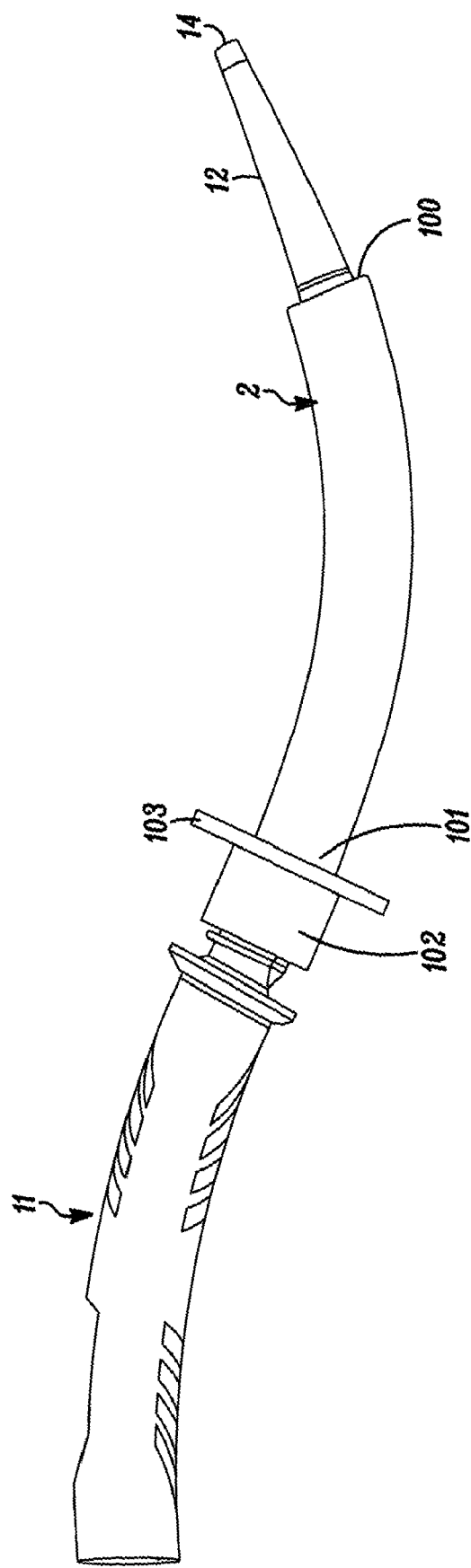
FIG. 3 is a side elevation view of an assembly of introducer and a tracheostomy tube.

FIG. 3 shows an assembly of the introducer 1 with a conventional tracheostomy tube 2 of the kind having a patient end 100 adapted to be located within the trachea and a machine end 101 adapted to project externally from the neck surface. The machine end 101 of the tube 2 has a conventional 15 mm female hub or connector 102 by which connection is made to the tube, and a flange 103 to which a neck strap (not shown) can be attached in order to secure the tube about the patient's neck. The tube 2 could be provided with a conventional inflatable sealing cuff close to its patient end but is shown as being without any such cuff.

The tracheostomy tube 2 is introduced by first surgically forming a passage from the skin surface of the neck through neck tissue into the trachea in the usual way with a needle and guidewire. The needle is then removed to leave the guidewire in place extending along the passage with one end protruding externally. The passage is then dilated using one or more dilators. Next, the tube 2 is loaded onto the introducer 1 so that its connector 102 is fitted on the boss 18 and the nose portion 12 of the introducer projects out of the patient end 100 of the tube by a distance that is between 4-5 times the external diameter of the tube. The handle 21 of the introducer 1 is gripped by hand and the assembly is pushed along the guidewire through the tracheostomy opening until the flange 103 of the tube 2 lies against the skin surface of the neck and the patient end 100 of the tube lies in the trachea. The introducer 1 is then removed by pulling out rearwardly, leaving the tube 2 in position with its patient end in the trachea.

The S-bend shape of the introducer 1 gives it particular ergonomic advantages in enabling the relatively high insertion forces to be applied that are needed to insert the assembly while also enabling the application of this force to be carefully controlled.

Although the introducer of the present invention can be used to insert a tracheostomy tube along a passage dilated by any conventional dilator or series of dilators it has particular advantages when used in conjunction with a dilator having a similar S shape because the same insertion movements can be used by the surgeon to insert both the dilator and the introducer.

Figure 4:
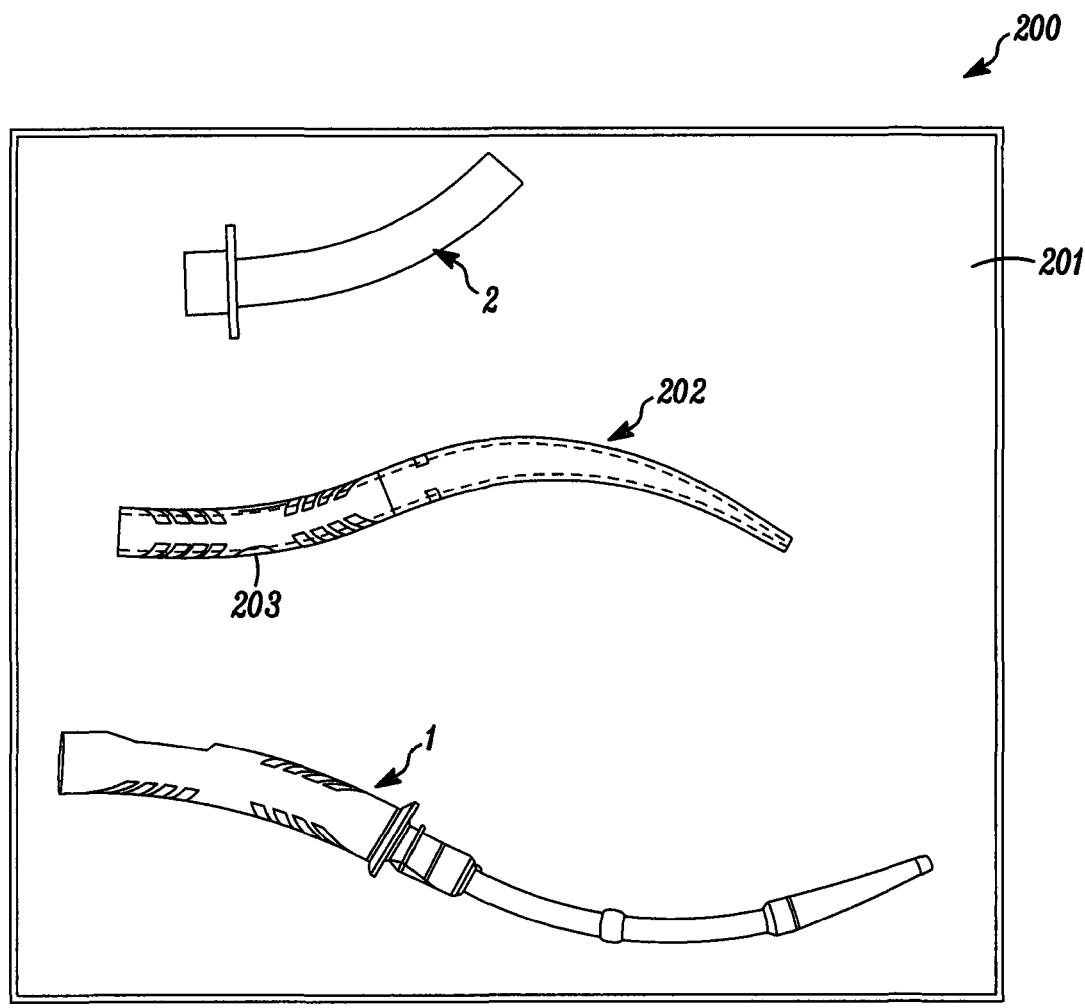
FIG. 4 is a schematic plan view of a tracheostomy kit including the introducer, tracheostomy tube and dilator.

FIG. 4 illustrates a preferred form of tracheostomy kit 200 comprising a packaging tray 201 containing the tracheostomy tube 2, the introducer 1 and a dilator 202. The dilator 202 is of the kind sold by Smiths Medical International Limited having an S shape along its length and a side opening 203 for a guidewire towards the rear end of the dilator. The kit 200 would contain other conventional components such as guidewire, needle, scalpel, neck tie, antiseptic wipes and the like.

The invention is not confined to use with tracheostomy tubes but could be used with other tubes for insertion in a body cavity.

The invention claimed is:

1. An introducer adapted for insertion within the bore of a tube having a patient end and a machine end, the introducer having a tapering patient end adapted to extend beyond the patient end of the tube and a machine end adapted to extend beyond the machine end of the tube to provide a machine end portion by which the introducer can be gripped when inserted in the tube, characterised in that at least a part of the introducer has an S shape with a patient end region curved in one sense and a machine end region forming a smoothly continuous curve with the patient end region but in the opposite sense, wherein the introducer has a side opening on the outside of the curve of the machine end portion and; wherein the introducer is rigid.

2. An introducer according to claim 1, characterised in that the introducer has a bore extending along a part of the length of the introducer and opening towards the machine end through the side opening.

3. An introducer according to claim 1, characterised in that the patient end region includes along most of its length a shaft with an enlarged portion at a location along its length to centralise the introducer within the bore of the tube in which it is inserted.

4. An assembly of a tracheostomy tube and an introducer inserted within the bore of the tube having a patient end and a machine end, the introducer having a tapering patient end adapted to extend beyond the patient end of the tube and a machine end adapted to extend beyond the machine end of the tube to provide a machine end portion by which the introducer can be gripped when inserted in the tube, at least a part of the introducer having an S shape with a patient end region curved in one sense and a machine end region forming a smoothly continuous curve with the patient end region but in the opposite sense, wherein the introducer has a bore extending from an opening at the patient end of the introducer to a side opening at the outside curve of the machine end portion of the introducer.

5. An assembly according to claim 4, wherein the tube is a tracheostomy tube.

6. A kit of components for use in a tracheostomy procedure including a tracheostomy tube having a patient end and a machine end, an introducer adapted for insertion within the bore of a medico-surgical tube, the introducer having a tapering patient end adapted to extend beyond the patient end of the tube and a machine end adapted to extend beyond the machine end of the tube to provide a machine end portion by which the introducer can be gripped when inserted in the tube, characterised in that at least a part of the introducer has an S shape with a patient end region curved in one sense and a machine end region forming a smoothly continuous curve with the patient end region but in the opposite sense, that the introducer has a side opening on the outside of the curve at the machine end portion that the introducer is rigid, and a dilator adapted to enlarge a passage into the trachea prior to insertion of an assembly of the tracheostomy tube and introducer, characterised in that the dilator has an S shape of the same general form as that of the introducer.

7. A method of introducing a tracheostomy tube including the steps of surgically forming a passage from the surface of the neck through neck tissue into the trachea, positioning a guide member to extend along the passage with one end protruding externally, sliding an S-shape dilator along the guide member to dilate the passage, removing the dilator, sliding an assembly along the guide member, the assembly having a medico-surgical tube and an introducer inserted in the tube, the introducer having a tapering patient end adapted to extend beyond the patient end of the tube and a machine end adapted to extend beyond the machine end of the tube to provide a machine end portion by which the introducer can be gripped when inserted in the tube, at least a part of the introducer having an S shape with a patient end region curved in one sense and a machine end region forming a smoothly continuous curve with the patient end region but in the opposite sense wherein the introducer is rigid, wherein the introducer has a bore extending between an opening at the patient end and a side opening on the outside of the curve at the machine end portion to enable the guide member to extend along the introducer so that the assembly can be slid along the guide member to insert the tube into the trachea of the patient, and then removing the introducer and guide member to leave the tube in position with its patient end in the trachea.

8. The kit of claim 6, wherein the side opening extends to an opening at the patient end of the introducer through a bore that extends along a part of the introducer.

* * * * *